US010852269B2

(12) United States Patent
Yamada et al.

(10) Patent No.: US 10,852,269 B2
(45) Date of Patent: Dec. 1, 2020

(54) GAS SENSOR

(71) Applicant: NGK Spark Plug Co., Ltd., Nagoya (JP)

(72) Inventors: Tetsuo Yamada, Nagoya (JP); Hitoshi Furuta, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 66 days.

(21) Appl. No.: 16/417,893

(22) Filed: May 21, 2019

(65) Prior Publication Data

US 2019/0360961 A1    Nov. 28, 2019

(30) Foreign Application Priority Data

May 25, 2018   (JP) .................... 2018-100595

(51) Int. Cl.
*G01N 27/407*    (2006.01)
*G01N 33/00*    (2006.01)
*G01N 27/416*    (2006.01)

(52) U.S. Cl.
CPC ..... *G01N 27/4076* (2013.01); *G01N 27/4071* (2013.01); *G01N 27/416* (2013.01); *G01N 33/0054* (2013.01)

(58) Field of Classification Search
None
See application file for complete search history.

(56) References Cited

U.S. PATENT DOCUMENTS

2017/0227490 A1    8/2017  Nakano et al.

FOREIGN PATENT DOCUMENTS

JP          2017-142243 A        8/2017

*Primary Examiner* — J. Christopher Ball
(74) *Attorney, Agent, or Firm* — Stites & Harbison, PLLC; Jeffrey A. Haeberlin (57) ABSTRACT

A gas sensor for detecting the concentration of a detection target gas in an atmosphere of interest is disposed on an electrically insulating member. The gas sensor includes an insulating porous layer formed of an electrically insulating porous material, a reference electrode, a solid electrolyte body, a detection electrode that are stacked in this order on the electrically insulating member, and a reference electrode lead disposed between the insulating member and the insulating porous layer. The insulating porous layer defines a through hole in a region sandwiched between the reference electrode lead and the reference electrode. An electrically conductive member formed of a material having electrical conductivity is disposed in the through hole so as to extend from an opening of the through hole at one end thereof to an opening of the through hole at the other end thereof.

2 Claims, 6 Drawing Sheets

GAS SENSOR

CROSS REFERENCE TO RELATED APPLICATION

The present application claims priority to Japanese Patent Application No. 2018-100595, which was filed on May 25, 2018, the disclosure of which is herein incorporated by reference in its entirety.

BACKGROUND OF THE INVENTION

Field of the Invention

The present disclosure relates to a gas sensor that detects the concentration of a gas present in an atmosphere of interest.

Description of Related Art

Patent Document 1 describes a gas sensor that is disposed on an electrically insulating member, has a structure including an insulating porous layer, a reference electrode, a solid electrolyte body, and a detection electrode that are stacked in this order on the electrically insulating member, and detects the concentration of a detection target gas in an atmosphere of interest.

Related Art Document

Patent Document 1 is Japanese Patent Application Laid-Open (kokai) No. 2017-142243.

BRIEF SUMMARY OF THE INVENTION

In the gas sensor described in Patent Document 1, since the insulating porous layer is stacked on the insulating member, a step is formed between the surface of the insulating member and the surface of the insulating porous layer. A reference electrode lead electrically connected to the reference electrode is formed on the surface of the insulating member. Specifically, the reference electrode lead is formed so as to extend over and across the step, and the reference electrode stacked on the insulating porous layer is thereby connected to the reference electrode lead formed on the surface of the insulating member. However, when the reference electrode lead is formed in the manner described above, a step is also formed on the reference electrode lead, and the reference electrode lead becomes more likely to break at the step.

It is an object of the present disclosure to prevent the occurrence of breakage of the reference electrode lead.

One mode of the present disclosure is a gas sensor that detects the concentration of a detection target gas in an atmosphere of interest, the gas sensor being disposed on an electrically insulating member and including an insulating porous layer formed of an electrically insulating porous material, a reference electrode, a solid electrolyte body, and a detection electrode that are stacked in this order on the electrically insulating member.

The gas sensor includes a reference electrode lead disposed between the insulating member and the insulating porous layer. The insulating porous layer has a through hole that is formed in a region sandwiched between the reference electrode lead and the reference electrode and extends through the insulating porous layer. In other words, the insulating porous layer defines a through hole in a region sandwiched between the reference electrode lead and the reference electrode, the through hole extending through the insulating porous layer. An electrically conductive member formed of a material having electrical conductivity is disposed in (inside) the through hole so as to extend from an opening of the through hole at one end thereof to an opening of the through hole at the other end thereof, thereby electrically connecting the reference electrode lead and the reference electrode through the electrically conductive member.

In the gas sensor of the present disclosure having the above structure, the reference electrode lead is electrically connected to the reference electrode with the reference electrode lead disposed between the insulating member and the insulating porous layer. Therefore, in the gas sensor of the present disclosure, the reference electrode lead does not extend over and across the step formed between the surface of the insulating member and the surface of the insulating porous layer. In the gas sensor of the present disclosure, the occurrence of breakage of the reference electrode lead can thereby be prevented.

In the one mode of the present disclosure, the through hole may be disposed such that an orthogonal projection of the through hole onto a reference plane perpendicular to a direction of stacking of the insulating porous layer, the reference electrode, the solid electrolyte body, and the detection electrode does not overlap an orthogonal projection of the detection electrode onto the reference plane.

Therefore, in the gas sensor of the present disclosure, an end portion of the reference electrode lead is not disposed below a region in which the detection electrode is formed (hereinafter referred to as a detection electrode-formed region). Specifically, in the gas sensor of the present disclosure, the step formed between the surface of the insulating member and the surface of the reference electrode lead is not located below the detection electrode-formed region. Therefore, in the gas sensor of the present disclosure, the occurrence of unevenness in thickness in a region in which the insulating porous layer, the reference electrode, the solid electrolyte body, and the detection electrode are stacked can be prevented.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

An embodiment of the present disclosure will be described with reference to the drawings.

A multi-gas detector in the present embodiment is used for a urea SCR system that is mounted on a vehicle to clean nitrogen oxide (NOx)-containing exhaust gas emitted from a diesel engine. The SCR is an abbreviation of Selective Catalytic Reduction. More specifically, the multi-gas detector measures, after the NOx contained in the exhaust gas is reacted with ammonia, the concentrations of nitrogen monoxide (NO), nitrogen dioxide ($NO_2$), and ammonia contained in the resulting exhaust gas. The vehicle on which the multi-gas detector is mounted is referred to as the "present vehicle."

Figure 1:
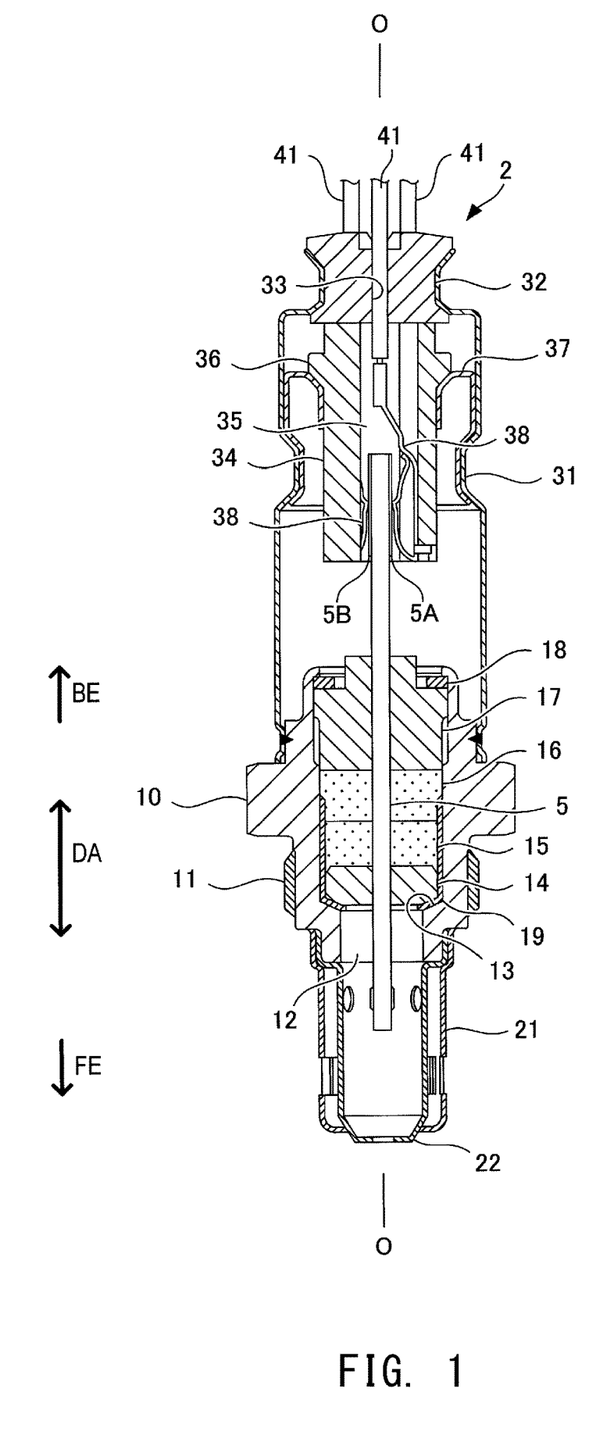
FIG. 1 is a cross-sectional view showing the internal structure of a multi-gas sensor.
Figure 2:
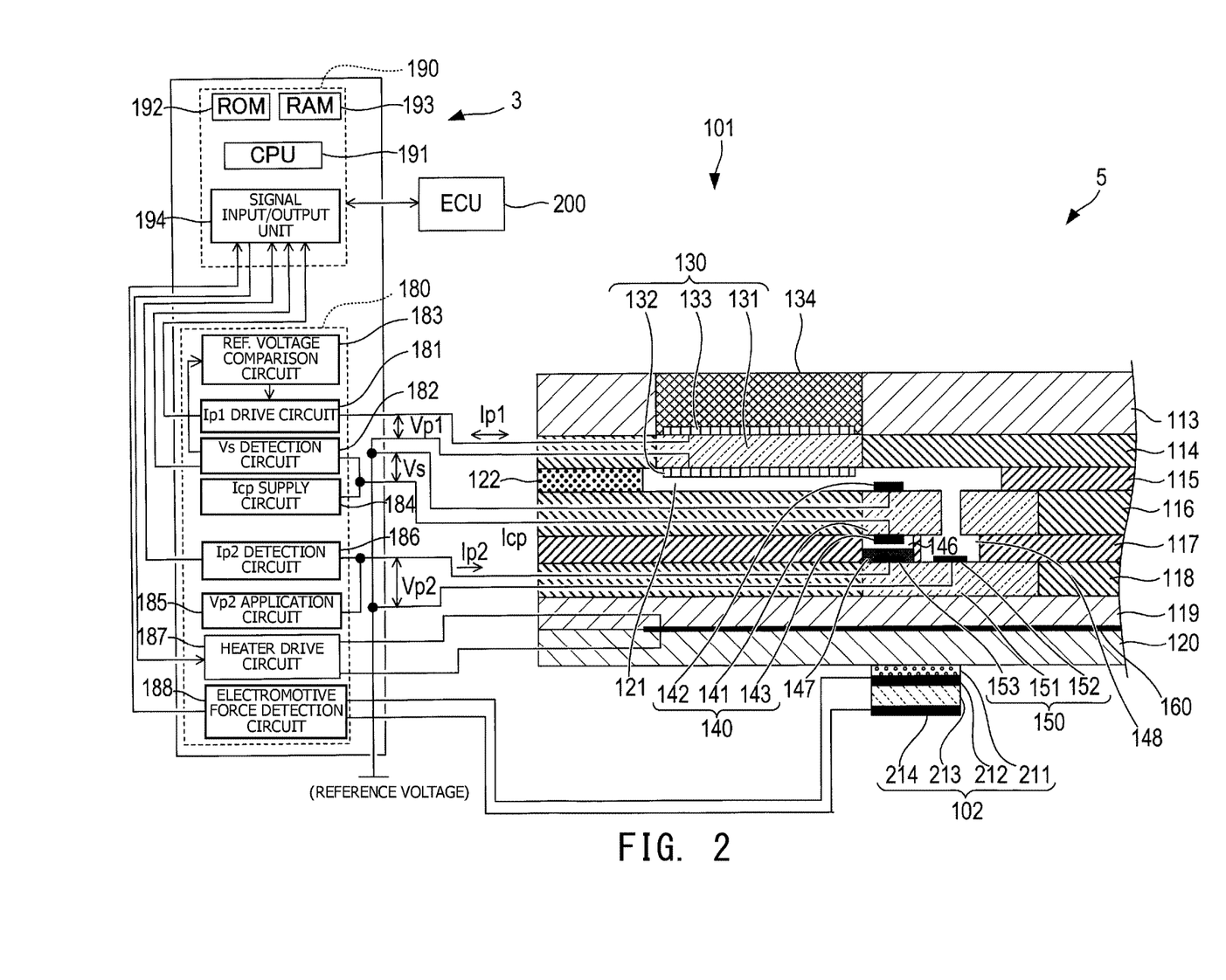
FIG. 2 is a schematic illustration of the structure of a sensor element unit and the configuration of a controller.

The multi-gas detector includes a multi-gas sensor 2 shown in FIG. 1 and a controller 3 shown in FIG. 2.

As shown in FIG. 1, the multi-gas sensor 2 includes a sensor element unit 5, a metallic shell 10, a separator 34, and connection terminals 38. In the following description, the side of the multi-gas sensor 2 on which the sensor element unit 5 is disposed (i.e., the lower side in FIG. 1) is referred to as a forward end side FE, and the side on which the connection terminals 38 are disposed (i.e., the upper side in FIG. 1) is referred to as a rear end side BE.

The sensor element unit 5 has a plate shape and extends in the direction of an axial line O (hereinafter referred to as an axial direction DA). Electrode terminals 5A and 5B are disposed at the rear end of the sensor element unit 5. In FIG. 1, only the electrode terminals 5A and 5B are shown as electrode terminals formed on the sensor element unit 5 for the purpose of simplifying the drawing. However, in actuality, the number of the electrode terminals is determined in accordance with the number of, for example, electrodes provided in an NOx detection section 101 and an ammonia detection section 102 described later.

The metallic shell 10 is a tubular member, and a threaded portion 11 used to fix the multi-gas sensor 2 to an exhaust pipe of a diesel engine is formed on the external surface of the metallic shell 10. The metallic shell 10 has a through hole 12 extending in the axial direction DA and a ledge 13 protruding inward in the radial direction of the through hole 12. The ledge 13 has as an inward taper surface inclined such that its position gradually shifts toward the forward end side FE while extending from the radially outer side of the through hole 12 toward its center.

The metallic shell 10 holds the sensor element unit 5 such that a portion of the sensor element unit 5 on the forward end side FE protrudes from the through hole 12 toward the forward end side FE and a portion of the sensor element unit 5 on the rear end side BE protrudes from the through hole 12 toward the rear end side BE.

A ceramic holder 14 that is a tubular member surrounding the circumference of the sensor element unit 5, talc rings 15 and 16 that are layers of charged talc powder, and a ceramic sleeve 17 are stacked in this order inside the through hole 12 of the metallic shell 10 from the forward end side FE toward the rear end side BE.

A crimp packing 18 is disposed between the ceramic sleeve 17 and a rear end portion of the metallic shell 10. A metallic holder 19 is disposed between the ceramic holder 14 and the ledge 13 of the metallic shell 10. The metallic holder 19 holds the talc ring 15 and the ceramic holder 14. The rear end portion of the metallic shell 10 is crimped so as to press the ceramic sleeve 17 toward the forward end side FE through the crimp packing 18.

An outer protector 21 and an inner protector 22 are provided at a forward end portion of the metallic shell 10. The outer protector 21 and the inner protector 22 are tubular members formed from a metallic material such as stainless steel and each having a closed forward end. The inner protector 22 covers a forward end portion of the sensor element unit 5 and is welded to the metallic shell 10, and the outer protector 21 covers the inner protector 22 and is welded to the metallic shell 10.

A forward end portion of an outer tube 31 formed into a tubular shape is fixed to the rear end portion of the metallic shell 10. A grommet 32 is disposed in a rear end opening of the outer tube 31 so as to close the opening.

Lead wire insertion holes 33 into which lead wires 41 are inserted are formed in the grommet 32. The lead wires 41 are electrically connected to the electrode terminals 5A and 5B of the sensor element unit 5.

The separator 34 is a tubular member disposed on the rear end side BE of the sensor element unit 5. A space formed inside the separator 34 is an insertion hole 35 extending through the separator 34 in the axial direction DA. A flange portion 36 protrudes radially outward from the outer surface of the separator 34.

A rear end portion of the sensor element unit 5 is inserted into the insertion hole 35 of the separator 34, and the electrode terminals 5A and 5B are disposed inside the separator 34.

A tubular holding member 37 is disposed between the separator 34 and the outer tube 31. The holding member 37 is in contact with the flange portion 36 of the separator 34 and also with the inner surface of the outer tube 31 and thereby holds the separator 34 such that the separator 34 is fixed to the outer tube 31.

The connection terminals 38 are members disposed inside the insertion hole 35 of the separator 34 and are electrically conductive members that electrically connect the electrode terminals 5A and 5B of the sensor element unit 5 to their respective lead wires 41. In FIG. 1, only two connection terminals 38 are shown for the purpose of simplifying the drawing.

As shown in FIG. 2, the controller 3 of the multi-gas detector is electrically connected to an electronic control unit 200 mounted on the present vehicle. The electronic control unit 200 receives data representing the concentrations of NO, $NO_2$, and ammonia in exhaust gas that are computed by the controller 3. Then the electronic control unit 200 performs processing for controlling the operating conditions of the diesel engine according to the data received and also performs cleaning processing for NOx accumulated on a catalyst.

The sensor element unit 5 includes the NOx detection section 101 and the ammonia detection section 102.

The NOx detection section 101 is formed by sequentially stacking an insulating layer 113, a ceramic layer 114, an insulating layer 115, a ceramic layer 116, an insulating layer 117, a ceramic layer 118, an insulating layer 119, and an insulating layer 120. The insulating layers 113, 115, 117, 119, and 120 are formed mainly of alumina.

The NOx detection section 101 includes a first measurement chamber 121 formed between the ceramic layer 114 and the ceramic layer 116. In the NOx detection section 101, the exhaust gas is introduced from the outside into the interior of the first measurement chamber 121 through a diffusion resistor 122 that is disposed between the ceramic layer 114 and the ceramic layer 116 so as to be adjacent to the first measurement chamber 121. The diffusion resistor 122 is formed of a porous material such as alumina.

The NOx detection section 101 further includes a first pumping cell 130. The first pumping cell 130 includes a solid electrolyte layer 131 and pumping electrodes 132 and 133.

The solid electrolyte layer 131 is formed mainly of zirconia having oxygen ion conductivity. A part of the ceramic layer 114 is removed from a region exposed to the first measurement chamber 121, and the resulting space is filled with the solid electrolyte layer 131 instead of the ceramic layer 114.

The pumping electrodes 132 and 133 are formed mainly of platinum. The pumping electrode 132 is disposed on the solid electrolyte layer 131 so as to be exposed to the first measurement chamber 121. The pumping electrode 133 is disposed on the solid electrolyte layer 131 on the side opposite the pumping electrode 132 with the solid electrolyte layer 131 sandwiched between the pumping electrodes 132 and 133. The insulating layer 113 is removed from a region in which the pumping electrode 133 is disposed and from a region around the pumping electrode 133, and the resulting space is filled with a porous material 134 instead of the insulating layer 113. The porous material 134 allows oxygen migration between the pumping electrode 133 and the outside.

The NOx detection section 101 further includes an oxygen concentration detection cell 140. The oxygen concentration detection cell 140 includes a solid electrolyte layer 141, a detection electrode 142, and a reference electrode 143.

The solid electrolyte layer 141 is formed mainly of zirconia having oxygen ion conductivity. A part of the ceramic layer 116 is removed from a region rearward of the solid electrolyte layer 131, and the resulting space is filled with the solid electrolyte layer 141 instead of the ceramic layer 116.

The detection electrode 142 and the reference electrode 143 are formed mainly of platinum. The detection electrode 142 is disposed on the solid electrolyte layer 141 so as to be exposed to the first measurement chamber 121. The reference electrode 143 is disposed on the solid electrolyte layer 141 on the side opposite the detection electrode 142 with the solid electrolyte layer 141 sandwiched between the detection electrode 142 and the reference electrode 143.

The NOx detection section 101 further includes a reference oxygen chamber 146. The reference oxygen chamber 146 is a through hole formed by removing the insulating layer 117 from a region in which the reference electrode 143 is disposed and from a region around the reference electrode 143.

The NOx detection section 101 further includes a second measurement chamber 148. The second measurement chamber 148 is formed rearward of the detection electrode 142 and the reference electrode 143 so as to extend through the solid electrolyte layer 141 and the insulating layer 117. In the NOx detection section 101, the exhaust gas discharged from the first measurement chamber 121 is introduced into the second measurement chamber 148.

The NOx detection section 101 further includes a second pumping cell 150. The second pumping cell 150 includes a solid electrolyte layer 151 and pumping electrodes 152 and 153.

The solid electrolyte layer 151 is formed mainly of zirconia having oxygen ion conductivity. The ceramic layer 118 is removed from a region exposed to the reference oxygen chamber 146 and the second measurement chamber 148 and a region around this exposed region, and the resulting space is filled with the solid electrolyte layer 151 instead of the ceramic layer 118.

The pumping electrodes 152 and 153 are formed mainly of platinum. The pumping electrode 152 is disposed on the solid electrolyte layer 151 so as to be exposed to the second measurement chamber 148. The pumping electrode 153 is disposed on the solid electrolyte layer 151 so as to be opposed to the reference electrode 143 with the reference oxygen chamber 146 therebetween. A porous material 147 is disposed inside the reference oxygen chamber 146 so as to cover the pumping electrode 153.

The NOx detection section 101 further includes a heater 160. The heater 160 is a heat-generating resistor that is formed mainly of platinum and generates heat when energized and is disposed between the insulating layers 119 and 120.

The ammonia detection section 102 is formed on the outer surface of the NOx detection section 101, more specifically on the insulating layer 120. The ammonia detection section 102 is disposed at substantially the same position, with respect to the axial direction DA (i.e., the horizontal direction in FIG. 2), as the reference electrode 143 in the NOx detection section 101.

The ammonia detection section 102 has a structure formed by stacking a porous layer 211, a reference electrode 212, a solid electrolyte body 213 for ammonia, and detection electrodes 214 in this order.

The porous layer 211 is formed of the same material as the material of the porous material 134 and is disposed in contact with the surface of the insulating layer 120.

The reference electrode 212 is formed mainly of platinum (Pt) serving as an electrode material and more specifically formed of a material containing Pt and zirconium oxide ($ZrO_2$). The solid electrolyte body 213 for ammonia is formed of an oxygen ion-conductive material such as yttria-stabilized zirconia (YSZ). The reference electrode 212 is a dense layer having a smaller porosity than the porous layer 211. The detection electrodes 214 are formed mainly of gold (Au) serving as an electrode material and more specifically formed of a material containing Au and zirconium oxide ($ZrO_2$).

Therefore, a three-phase boundary at which ammonia comes into contact with the reference electrode 212 and the solid electrolyte body 213 for ammonia is formed at the interface between the reference electrode 212 and the solid electrolyte body 213 for ammonia. Similarly, another three-phase boundary at which ammonia comes into contact with the detection electrodes 214 and the solid electrolyte body 213 for ammonia is formed at the interface between the solid electrolyte body 213 for ammonia and the detection electrodes 214.

The controller 3 includes a control circuit 180 and a microcomputer 190.

The control circuit 180 is an analog circuit disposed on a circuit board. The control circuit 180 includes an Ip1 drive circuit 181, a Vs detection circuit 182, a reference voltage comparison circuit 183, an Icp supply circuit 184, a Vp2 application circuit 185, an Ip2 detection circuit 186, a heater drive circuit 187, and an electromotive force detection circuit 188.

The pumping electrode 132, the detection electrode 142, and the pumping electrode 152 are connected to a reference potential. The pumping electrode 133 is connected to the Ip1 drive circuit 181. The reference electrode 143 is connected to the Vs detection circuit 182 and the Icp supply circuit 184. The pumping electrode 153 is connected to the Vp2 application circuit 185 and the Ip2 detection circuit 186. The heater 160 is connected to the heater drive circuit 187.

The Ip1 drive circuit 181 applies a voltage Vp1 between the pumping electrode 132 and the pumping electrode 133 to supply a first pumping current Ip1 and detects the supplied first pumping current Ip1.

The Vs detection circuit 182 detects the voltage Vs between the detection electrode 142 and the reference electrode 143 and outputs the detection result to the reference voltage comparison circuit 183.

The reference voltage comparison circuit 183 compares a reference voltage (e.g., 425 mV) with the output from the Vs detection circuit 182 (i.e., the voltage Vs) and outputs the comparison result to the Ip1 drive circuit 181. The Ip1 drive circuit 181 controls the flow direction and magnitude of the first pumping current Ip1 such that the voltage Vs becomes equal to the reference voltage to thereby adjust the concentration of oxygen in the first measurement chamber 121 to a prescribed level at which decomposition of NOx does not occur.

The Icp supply circuit 184 causes a weak current Icp to flow between the detection electrode 142 and the reference electrode 143. Oxygen is thereby fed from the first measurement chamber 121 to the reference oxygen chamber 146 through the solid electrolyte layer 141, and the concentration of oxygen in the reference oxygen chamber 146 is set to be a prescribed oxygen concentration serving as a reference.

The Vp2 application circuit 185 applies a constant voltage Vp2 (e.g., 450 mV) between the pumping electrode 152 and the pumping electrode 153. As a result, in the second measurement chamber 148, NOx is dissociated (reduced) through the catalytic action of the pumping electrodes 152 and 153 included in the second pumping cell 150. The oxygen ions obtained as a result of the dissociation migrate in the solid electrolyte layer 151 between the pumping electrode 152 and the pumping electrode 153, so that a second pumping current Ip2 flows. The Ip2 detection circuit 186 detects the second pumping current Ip2.

The heater drive circuit 187 applies a positive voltage for energizing the heater 160 to one end of the heater 160, which is a heat-generating resistor, and applies a negative voltage for energizing the heater 160 to the other end of the heater 160 to thereby drive the heater 160.

The electromotive force detection circuit 188 detects the electromotive force between the reference electrode 212 and the detection electrodes 214 (hereinafter referred to as an ammonia electromotive force EMF) and outputs a signal representing the detection result to the microcomputer 190.

The microcomputer 190 includes a CPU 191, a ROM 192, a RAM 193, and a signal input/output unit 194.

The CPU 191 executes a process for controlling the sensor element unit 5 according to a program stored in the ROM 192. The signal input/output unit 194 is connected to the Ip1 drive circuit 181, the Vs detection circuit 182, the Ip2 detection circuit 186, the heater drive circuit 187, and the electromotive force detection circuit 188. The CPU 191 outputs a driving signal to the heater drive circuit 187 through the signal input/output unit 194 to control the heater 160.

The CPU 191 executes a process for removing the influence of the oxygen concentration from the value of the second pumping current Ip2 and from the ammonia electromotive force EMF on the basis of various data stored in the ROM 192 and further executes a process for computing NOx concentrations such as the concentration of NO and the concentration of $NO_2$ and the concentration of ammonia. No particular limitation is imposed on these processes, and processes described in, for example, Japanese Patent Application Laid-Open (kokai) No. 2011-075546 may be used.

Next, a method for producing the ammonia detection section 102 will be described.

Figure 4:
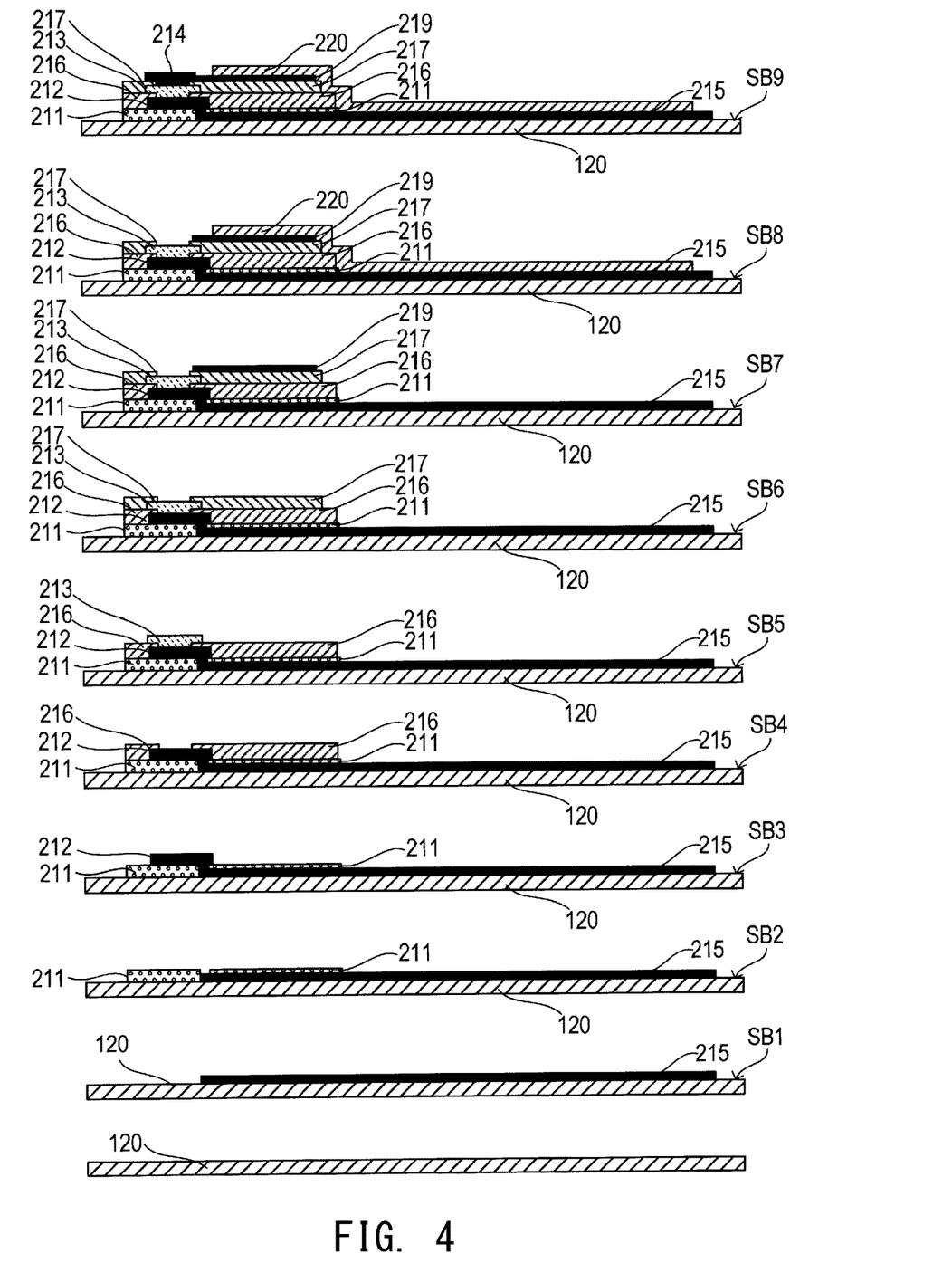
FIG. 4 is a schematic diagram showing cross sections of stacks in different production steps.
Figure 5:
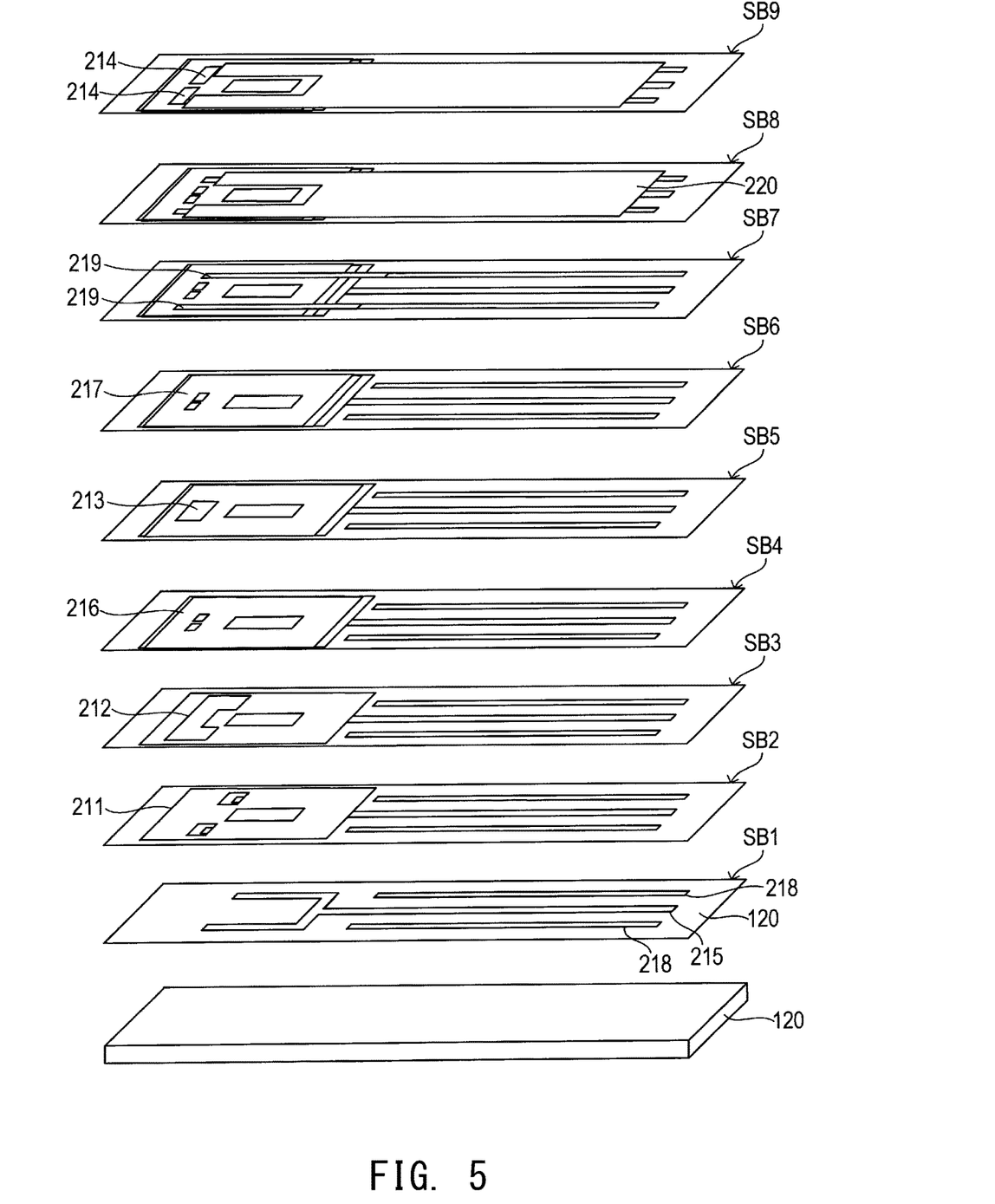
FIG. 5 is a schematic diagram showing surfaces of the stacks in different production steps.

First, as shown in a cross section of a stack SB1 in FIG. 4 and a surface of the stack SB1 in FIG. 5, a reference electrode lead pattern that later becomes a reference electrode lead 215 and a first detection electrode lead pattern that later becomes first detection electrode leads 218 are formed on the surface of a green insulating layer sheet that later becomes the insulating layer 120 of the NOx detection section 101. The reference electrode lead pattern and the first detection electrode lead pattern are formed by printing (e.g., screen printing) with a platinum paste containing platinum (Pt), zirconium oxide ($ZrO_2$), a binder, and an organic solvent.

Figure 3:
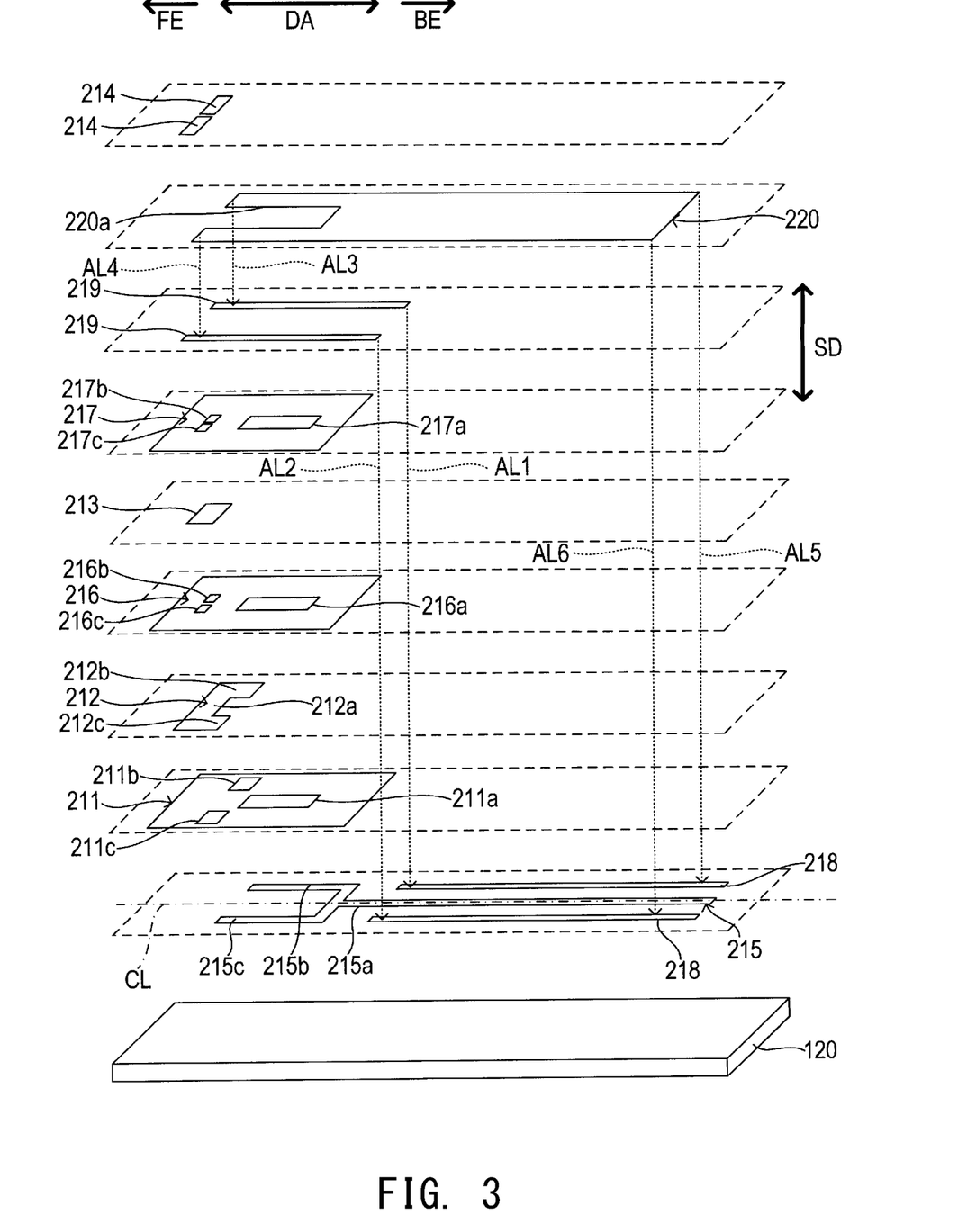
FIG. 3 is an exploded perspective view of an ammonia detection section.

As shown in FIG. 3, the reference electrode lead 215 includes a straight portion 215a and branched portions 215b and 215c. The straight portion 215a is formed so as to extend straight from a rear end portion of the sensor element unit 5 toward the forward end side FE. The branched portions 215b and 215c are formed so as to extend straight from the forward end of the straight portion 215a toward the forward end side FE. The branched portions 215b and 215c are disposed on first and second sides, respectively, of a center line CL which passes through the forward end of the straight portion 215a and is parallel to the axial direction DA.

The two first detection electrode leads 218 are formed so as to extend straight from a rear end portion of the sensor element unit 5 toward the forward end side FE. The forward ends of the first detection electrode leads 218 are located rearward of the forward end of the straight portion 215a. The two first detection electrode leads 218 are disposed on the first and seconds sides, respectively, of the center line CL.

As shown in a cross section of a stack SB2 in FIG. 4 and a surface of the stack SB2 in FIG. 5, a porous layer pattern that later becomes the porous layer 211 is formed on part of the surface of the green insulating layer sheet that later becomes the insulating layer 120 and on part of the surface of the reference electrode lead pattern. The porous layer pattern is formed by printing with a paste containing alumina, carbon, a binder, and an organic solvent.

As shown in FIG. 3, the porous layer 211 is formed into a rectangular shape. The forward end of the porous layer 211 is located forward of the forward end of the reference electrode lead 215. The rear end of the porous layer 211 is located forward of the forward ends of the first detection electrode leads 218.

Through holes 211a, 211b, and 211c are formed in the porous layer 211. The through hole 211a is located at a position corresponding to a region sandwiched between the branched portions 215b and 215c of the reference electrode lead 215. The through hole 211b is located at a position corresponding to the forward end of the branched portion 215b. The through hole 211c is located at a position corresponding to the forward end of the branched portion 215c.

Next, as shown in a cross section of a stack SB3 in FIG. 4 and a surface of the stack SB3 in FIG. 5, a reference electrode pattern that later becomes the reference electrode 212 is formed on part of the surface of the porous layer pattern. The reference electrode pattern is formed by printing with a reference electrode platinum paste containing platinum (Pt), zirconium oxide ($ZrO_2$), a binder, and an organic solvent. The reference electrode platinum paste differs from the above-mentioned lead pattern platinum paste in, for example, the diameter of platinum particles and the ratio of platinum to zirconium oxide. As shown in FIG. 3, the reference electrode 212 includes a connection portion 212a and cover portions 212b and 212c. The connection portion 212a connects the cover portion 212b and the cover portion 212c together. The cover portions 212b and 212c cover the through holes 211b and 211c, respectively.

Next, as shown in a cross section of a stack SB4 in FIG. 4 and a surface of the stack SB4 in FIG. 5, a first insulating layer pattern that later becomes a first insulating layer 216 is formed on the porous layer pattern and the reference electrode pattern. The first insulating layer pattern is formed by printing with a paste containing alumina, a binder, and an organic solvent.

As shown in FIG. 3, the first insulating layer 216 is formed into a rectangular shape. The forward end of the first insulating layer 216 is located forward of the forward end of the reference electrode lead 215. The rear end of the first insulating layer 216 is located forward of the forward ends of the first detection electrode leads 218.

Through holes 216a, 216b, and 216c are formed in the first insulating layer 216. The through hole 216a is located at a position corresponding to the region sandwiched between the branched portions 215b and 215c of the reference electrode lead 215. The through holes 216b and 216c are located at positions corresponding to the connection portion 212a of the reference electrode 212. The through holes 216b and 216c are located on first and second sides, respectively, of a plane including the center line CL and parallel to a stacking direction SD. The stacking direction SD is a direction of stacking of the porous layer 211, the reference electrode 212, the solid electrolyte body 213 for ammonia, and the detection electrodes 214.

Next, as shown in a cross section of a stack SB5 in FIG. 4 and a surface of the stack SB5 in FIG. 5, a solid electrolyte body pattern that later becomes the solid electrolyte body 213 for ammonia is formed on part of the surface of the first insulating layer pattern. The solid electrolyte body pattern is formed by printing with a paste containing a binder, an organic solvent, and an oxide powder that is a component of the solid electrolyte body. As shown in FIG. 3, the solid electrolyte body 213 for ammonia is formed into a rectangular shape. The solid electrolyte body 213 for ammonia is disposed so as to cover the through holes 216b and 216c.

Next, as shown in a cross section of a stack SB6 in FIG. 4 and a surface of the stack SB6 in FIG. 5, a second insulating layer pattern that later becomes a second insulating layer 217 is formed on the surface of the first insulating layer pattern and on the surface of the solid electrolyte body pattern. The second insulating layer pattern is formed by printing with a paste containing alumina, a binder, and an organic solvent.

As shown in FIG. 3, the second insulating layer 217 is formed into a rectangular shape. The forward end of the second insulating layer 217 is located forward of the forward end of the reference electrode lead 215. The rear end of the second insulating layer 217 is located forward of the forward ends of the first detection electrode leads 218.

Through holes 217a, 217b, and 217c are formed in the second insulating layer 217. The through hole 217a is located at a position corresponding to the region sandwiched between the branched portions 215b and 215c of the reference electrode lead 215. The through holes 217b and 217c are located at positions corresponding to the through holes 216b and 216c of the first insulating layer 216 with the solid electrolyte body 213 for ammonia therebetween. The through holes 217b and 217c are located on the first and second sides, respectively, of the plane including the center line CL and parallel to the stacking direction SD.

Next, as shown in a cross section of a stack SB7 in FIG. 4 and a surface of the stack SB7 in FIG. 5, a second detection electrode lead pattern that later becomes second detection electrode leads 219 is formed on part of the surface of the second insulating layer pattern and on part of the surface of the first detection electrode lead pattern. The second detection electrode lead pattern is formed by printing with the lead pattern platinum paste described above.

As shown in FIG. 3, the two second detection electrode leads 219 are formed so as to extend straight toward the rear end side BE with their forward ends located at positions not rearward of the through holes 217b and 217c. The rear ends of the second detection electrode leads 219 are located rearward of the forward ends of the first detection electrode leads 218, as shown by arrows AL1 and AL2. The two second detection electrode leads 219 are disposed on the first and second sides, respectively, of the plane including the center line CL and parallel to the stacking direction SD.

Next, as shown in a cross section of a stack SB8 in FIG. 4 and a surface of the stack SB8 in FIG. 5, a third insulating layer pattern that later becomes a third insulating layer 220 is formed on the surface of the second detection electrode lead pattern except for its forward end portions and on the surfaces of the reference electrode lead pattern and the first detection electrode lead pattern except for their rear end portions. The third insulating layer pattern is formed by printing with a paste containing alumina, a binder, and an organic solvent.

As shown in FIG. 3, the third insulating layer 220 is formed into a rectangular shape with part of its forward end cut away. The forward end of the third insulating layer 220 is located rearward of the forward ends of the second detection electrode leads 219, as shown by arrows AL3 and AL4. The rear end of the third insulating layer 220 is located forward of the rear ends of the reference electrode lead 215 and the first detection electrode leads 218, as shown by arrows AL5 and AL6. The cut-away portion 220a formed in the third insulating layer 220 is located at a position corresponding to the through hole 217a of the second insulating layer 217.

Then the stack SB8 is fired at a prescribed temperature (e.g., 1,500° C.).

Next, as shown in a cross section of a stack SB9 in FIG. 4 and a surface of the stack SB9 in FIG. 5, a detection electrode pattern that later becomes the detection electrodes 214 is formed on part of the surface of the second insulating layer 217 and on forward end portions of the surfaces of the second detection electrode leads 219. The detection electrode pattern is formed by printing with a gold paste containing gold (Au), zirconium oxide ($ZrO_2$), a binder, and an organic solvent.

As shown in FIG. 3, the two detection electrodes 214 are each formed into a rectangular shape. One of the two detection electrodes 214 is disposed so as to cover the through hole 217b and the forward end of one of the two second detection electrode leads 219. The other one of the two detection electrodes 214 is disposed so as to cover the through hole 217c and the forward end of the other one of the two second detection electrode leads 219.

Then the stack SB9 is fired at a prescribed temperature (e.g., 1,000° C.). The ammonia detection section 102 is thereby obtained.

Next, the structure of the ammonia detection section 102 will be described in detail.

Figure 6:
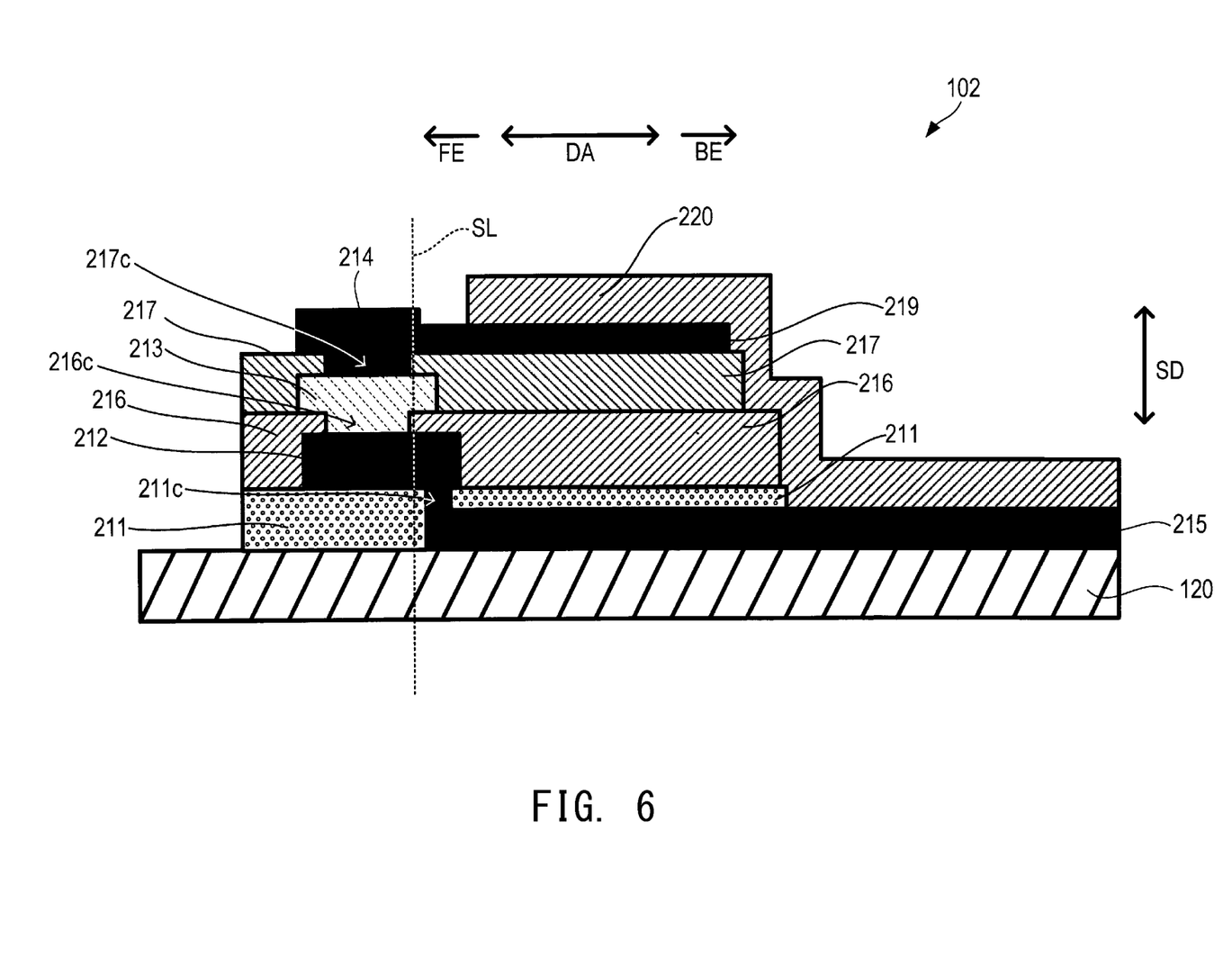
FIG. 6 is a cross-sectional view of an exemplary ammonia detection section according to the invention.

As shown in FIG. 6, the ammonia detection section 102 includes the porous layer 211, the reference electrode 212, the solid electrolyte body 213 for ammonia, and the detection electrodes 214, which are described above, as well as the reference electrode lead 215, the first insulating layer 216, the second insulating layer 217, the first detection electrode leads 218, the second detection electrode leads 219, and the third insulating layer 220.

The reference electrode lead 215 is disposed on the surface of the insulating layer 120. The porous layer 211 is disposed on the surface of the insulating layer 120 and on the surface of the reference electrode lead 215. The porous layer 211 has the through hole 211c formed at a position corresponding to the forward end of the reference electrode lead 215.

The reference electrode 212 is disposed on the surface of the porous layer 211 so as to cover the through hole 211c. The through hole 211c is thereby filled with the reference electrode 212, and the reference electrode 212 is electrically connected to the reference electrode lead 215.

The first insulating layer 216 is disposed on the surface of the porous layer 211 and on the surface of the reference electrode 212. The first insulating layer 216 has the through hole 216c formed at a position corresponding to the reference electrode 212.

The solid electrolyte body 213 for ammonia is disposed on the surface of the first insulating layer 216 so as to cover the through hole 216c. The through hole 216c is thereby filled with the solid electrolyte body 213 for ammonia, and the solid electrolyte body 213 for ammonia is brought into contact with the reference electrode 212.

The second insulating layer 217 is disposed on the surface of the first insulating layer 216 and on the surface of the solid electrolyte body 213 for ammonia. The second insulating layer 217 has the through hole 217c formed at a position corresponding to the solid electrolyte body 213 for ammonia.

The second detection electrode leads 219 are disposed on the surface of the second insulating layer 217. One of the detection electrodes 214 is disposed on the surface of the second insulating layer 217 so as to cover the through hole 217c and to be in contact with one of the second detection electrode leads 219. The through hole 217c is thereby filled with this detection electrode 214, and the detection electrode 214 is brought into contact with the solid electrolyte body 213 for ammonia. The through hole 211c is disposed so as not to be located on a straight line parallel to the stacking direction SD and passing through the detection electrode 214, as shown by, for example, straight line SL.

The above-configured ammonia detection section 102 is disposed on the electrically insulating layer 120 and has a structure including the porous layer 211 formed of an electrically insulating porous material, the reference electrode 212, the solid electrolyte body 213 for ammonia, and the detection electrodes 214 that are stacked in this order on the insulating layer 120. The ammonia detection section 102 detects the concentration of ammonia in the exhaust gas.

The ammonia detection section 102 includes the reference electrode lead 215 disposed between the insulating layer 120 and the porous layer 211. The through holes 211b and 211c extending through the porous layer 211 are formed in the porous layer 211 at positions sandwiched between the reference electrode lead 215 and the reference electrode 212. The reference electrode 212 is disposed inside the through holes 211b and 211c so as to extend from their openings on one side to the openings on the other side, and the reference electrode lead 215 is thereby electrically connected to the reference electrode 212.

As described above, in the ammonia detection section 102, the reference electrode lead 215 is electrically connected to the reference electrode 212 with the reference electrode lead 215 interposed between the insulating layer 120 and the porous layer 211. Therefore, in the ammonia detection section 102, the reference electrode lead 215 does not extend over and across the step formed between the surface of the insulating layer 120 and the surface of the porous layer 211. As a result, in the ammonia detection section 102, the occurrence of breakage of the reference electrode lead 215 can be prevented.

The through holes 211b and 211c are disposed such that their orthogonal projections onto a reference plane perpendicular to the stacking direction SD (the direction of stacking of the porous layer 211, the reference electrode 212, the solid electrolyte body 213 for ammonia, and the detection electrodes 214) do not overlap orthogonal projections of the detection electrodes 214 onto the reference plane.

Therefore, in the ammonia detection section 102, the end portions of the reference electrode lead 215 are not located below regions in which the detection electrodes 214 are formed (hereinafter referred to as detection electrode-formed regions). Specifically, in the ammonia detection section 102, steps formed between the surface of the insulating layer 120 and the surface of the reference electrode lead 215 are not located below the detection electrode-formed regions. Therefore, in the ammonia detection section 102, the occurrence of unevenness in thickness in a region in which the porous layer 211, the reference electrode 212, and the solid electrolyte body 213 for ammonia, and the detection electrodes 214 are stacked can be prevented.

In the embodiment descried above, the ammonia detection section 102 corresponds to the gas sensor in the claims, and the insulating layer 120 corresponds to the electrically insulating member in the claims. The porous layer 211 corresponds to the insulating porous layer in the claims, and the solid electrolyte body 213 for ammonia corresponds to the solid electrolyte body in the claims.

The exhaust gas corresponds to the atmosphere of interest in the claims, and ammonia corresponds to the detection target gas in the claims. The through holes 211b and 211c correspond to the through hole in the claims, and the reference electrode 212 corresponds to the electrically conductive member in the claims.

While the embodiment of the present disclosure has been described, the present disclosure is not limited to the embodiment, and the present disclosure can be embodied in various other forms.

For example, in the above embodiment, the ammonia detection section 102 having a stacked structure including the reference electrode 212, the solid electrolyte body 213 for ammonia, and the detection electrodes 214 detects the concentration of ammonia. However, the present disclosure is not limited to the gas sensor that detects the concentration of ammonia. Namely, the present disclosure is applicable to any gas sensor for detecting the concentration of a gas other than ammonia, so long as the gas sensor has a stacked structure including a reference electrode, a solid electrolyte body, and a detection electrode.

In the above embodiment, the ammonia detection section 102 is formed on the outer surface of the NOx detection section 101. However, the present disclosure is not limited to the ammonia detection section formed on the gas sensor. The ammonia detection section 102 may be formed on any electrically insulating member.

In the above embodiment, the reference electrode 212 is disposed inside the through holes 211b and 211c. However, it is only necessary that an electrically conductive member formed of a material having electrical conductivity be disposed inside the through holes 211b and 211c.

The function of one constituent element in the above embodiment may be distributed to a plurality of constituent elements, or the functions of a plurality of constituent elements may be realized by one constituent element. Part of the configurations of the above embodiment may be omitted. Also, at least part of the configuration of the above embodiment may be added to or partially replace the configurations of other embodiments. Notably, all modes included in the technical idea specified by the wording of the claims are embodiments of the present disclosure.

DESCRIPTION OF REFERENCE NUMERALS

102: ammonia detection section
120: insulating layer
211: porous layer
211b, 211c: through hole
212: reference electrode
213: solid electrolyte body for ammonia
214: detection electrode
215: reference electrode lead

What is claimed is:

1. A gas sensor that detects the concentration of a detection target gas in an atmosphere of interest, the gas sensor being disposed on an electrically insulating member and comprising:
    an insulating porous layer formed of an electrically insulating porous material, a reference electrode, a solid electrolyte body, and a detection electrode stacked in this order on the electrically insulating member,
    a reference electrode lead disposed between the electrically insulating member and the insulating porous layer,
    the insulating porous layer defining a through hole in a region sandwiched between the reference electrode lead and the reference electrode, the through hole extending through the insulating porous layer, and
    an electrically conductive member formed of a material having electrical conductivity disposed in the through hole so as to extend from an opening of the through hole at one end thereof to an opening of the through hole at the other end thereof, thereby electrically connecting the reference electrode lead and the reference electrode.

2. A gas sensor according to claim 1, wherein an orthogonal projection of the through hole onto a reference plane perpendicular to a direction of stacking of the insulating porous layer, the reference electrode, the solid electrolyte body, and the detection electrode does not overlap an orthogonal projection of the detection electrode onto the reference plane.

* * * * *